United States Patent [19]

Baumberg

[11] Patent Number: 4,898,164
[45] Date of Patent: Feb. 6, 1990

[54] AIR SUPPLYING DEVICE, AND METHOD OF AIR SUPPLY

[76] Inventor: Iosif Baumberg, 69 Bay 29 St., Brooklyn, N.Y.

[21] Appl. No.: 311,046

[22] Filed: Feb. 17, 1989

[51] Int. Cl.⁴ .............. A61M 16/20; A61M 15/00; A62B 7/00; A62B 7/12
[52] U.S. Cl. .............. 128/202.18; 128/204.18; 128/203.12; 5/434; 5/423
[58] Field of Search .............. 128/202.18, 204.18, 128/205.13, 205.16, 205.18; 5/434, 435, 441, 442, 423, 421, 468, 469

[56] References Cited

U.S. PATENT DOCUMENTS

| | | | |
|---|---|---|---|
| 2,025,659 | 12/1935 | Gilquin | 128/202.18 |
| 2,295,363 | 9/1942 | Schott | 5/434 |
| 2,315,391 | 3/1943 | Blair | 5/434 |
| 2,917,046 | 12/1959 | Fairbanks | 128/202.18 |
| 3,486,177 | 12/1969 | Marshack | 5/469 |
| 3,603,430 | 9/1971 | Kendall | 5/469 |
| 3,616,470 | 11/1971 | Young et al. | 5/435 |
| 3,653,083 | 4/1972 | Lapidus | 5/469 |
| 4,752,064 | 6/1988 | Voss | 5/435 |

FOREIGN PATENT DOCUMENTS 1420221  1/1976  United Kingdom .............. 5/434

Primary Examiner—Edgar S. Burr
Assistant Examiner—Kimberly L. Asher
Attorney, Agent, or Firm—Ilya Zborovsky

[57] ABSTRACT

Air is supplied directly to the area of a subject's nose and mouth when he or she lies on a pillow, through a device which has a plurality of inflatable valve-chambers located under the pillow, so that when the subject's head rests on one of the areas and on one of the valve-chambers the latter is deflated, while another valve-chamber is inflated to let the air from its associated passage exit through its associated outlet directly towards the subject's face.

9 Claims, 1 Drawing Sheet

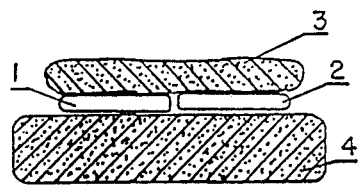
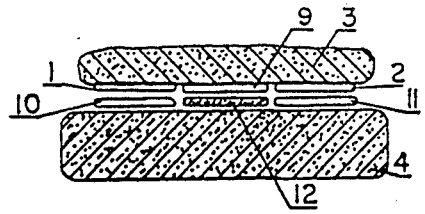
FIG.1  FIG.3
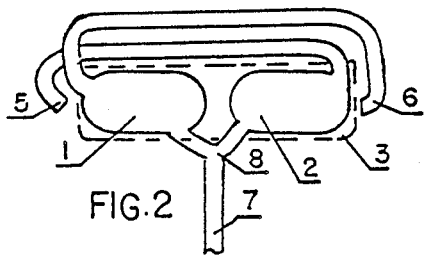
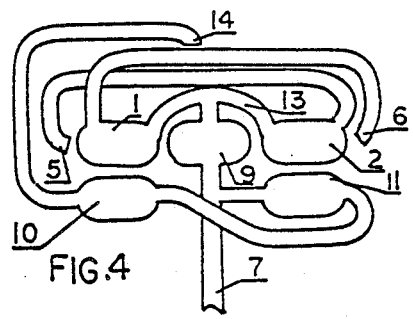
FIG.2  FIG.4
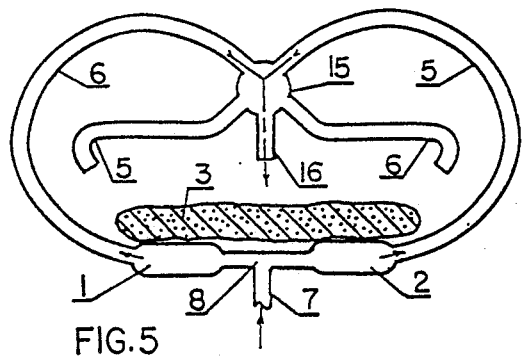
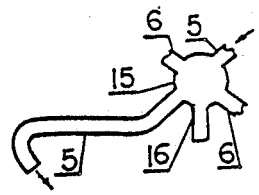
FIG.5  FIG.6
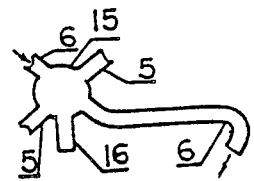
FIG.7

AIR SUPPLYING DEVICE, AND METHOD OF AIR SUPPLY

BACKGROUND OF THE INVENTION

The present invention relates to ventilating or air supplying devices, especially for households and medical purposes.

Ventilating devices are known, which include valves, faucets, flaps, etc. They are not designed so as to automatically direct an air stream with a small value of its cross section to a subject whose position varies in an unpredictable manner, for example to direct air to a sleeping person to the area of his or her nose and mouth. While the known ventilating devices ventilate a space as a whole, they do not directly remove the exhaled air from the vicinity of the subject's nose and mouth, and as a result a portion of the exhaled air which is poor on oxygen is again inhaled by the subject.

SUMMARY OF THE INVENTION

Accordingly, it is an object of the present invention to provide an air supplying device which avoids the disadvantages of the prior art.

More particularly, it is an object of the present invention to provide an air supplying device which efficiently removes the exhaled air from the vicinity of subject's mouth and nose and thereby increases the oxygen content in a newly inhaled portion of air.

It is also an object of the present invention to provide an air supplying device which operates efficiently with a very narrow air stream and thereby reduces noise and power consumption.

It is a further object of the invention to provide an air supplying device which automatically follows the varying positions of the subject for supplying air to the latter, as well as supplying moisture, other substances and the like, which can br entrained in the air stream.

In keeping with these objects and with others which will become apparent hereinafter, one feature of the present invention resides, briefly stated, in an air supplying device which has a plurality of normally inflated valve-chambers and a plurality of air passages connected with the valve-chambers and having outlets located at least at opposite sides of a pillow, so that when the valve-chambers are placed under the pillow and the subject rests on one of the valve-chambers the latter is deflated while another valve-chamber is inflated and discharges the supplied air through the outlet of its associated passage toward the subject's face.

When the air supplying device is designed in accordance with the present invention, it attains the abovespecified objects.

Actually, the area of the horizontal cross section of each of the valve-chambers is at most equal to the half of the area of the horizontal cross section of the pillow, while the area of the vertical cross section of the valve-chambers is not less than the area of the cross section of the passages.

The novel features of the present invention are set forth in the appended claims. The invention itself, however, will be best understood from the following description of preferred embodiments, which is accompanied by the following drawings.

BRIEF DESCRIPTION OF THE DRAWINGS

FIG. 1 is a vertical cross section of an air supplying device in accordance with the present invention;

FIG. 2 is a plan view of the air supplying device in accordance with the present invention as shown in FIG. 1;

FIG. 3 is a view showing a vertical cross section of an air supplying device in accordance with another embodiment of the present invention;

FIG. 4 is a plan view of the air supplying device of FIG. 3; and

FIGS. 5–7 are view showing an air supplying device in accordance with still a further embodiment.

DESCRIPTION OF PREFERRED EMBODIMENTS

An air supplying device in accordance with the first embodiment of the present invention has two valve-chambers 1 and 2 which are located between a pillow 3 and a mattress 4 on the left side and on the right side respectively. A passage 5 extends from the chamber 2 and has an outlet at the left end of the pillow, while a passage 6 extends from the chamber 1 and has an outlet at the right end of the pillow. The chambers 1 and 2 are supplied with air through a tee 8 from a passage 7.

An air supplying device in accordance with the second embodiment includes the above mentioned valve chambers 1 and 2 located under the pillow on the left side and on the right side, respectively, and in addition a valve-chamber 9 located in the center. The chambers 1, 2 and 9 form an upper layer of the chambers. In addition, a valve-chamber 10 is located under the valve chamber 1, and a valve-chamber 11 is located under the valve-chamber 2. A gasket 12 is located under the central valve-chamber 9 for maintaining the chambers of the upper layer at the same level. The chambers 1 and 10 form the left chamber row, while the chamber 2 and 11 form the right chamber row. The passage 7 is connected with the chambers 1 and 2 through the chamber 9 and a tee 13. The passage 7 is also connected with a passage 14 through the chambers 10 and 11 which are connected with one another in series. While the outlets of the passages 5 and 6 are located at the left end and the right end of the pillow, respectively, the outlet of the passage 14 is located centrally of the pillow.

The air supplying device in accordance with the present invention operates in the following manner:

It has been recognized that when a subject lies on his right side, his face is turned to the left side of the pillow and vice versa, while when a subject lies on his back, his head, as a rule, lies on the central part of the pillow. The valve-chambers are formed as bags of air-impermeable material (similar to a bag in a blood-measuring device) and are normally inflated. In other words, they are not compressed unded the weight of the pillow, and become compressed only under the weight of the head of a subject. When a subject lies on his left side and his face is on the right side of the pillow, the right valve-chamber 2 is closed and the air flow through the passage 7, the left valve-chamber 1 and the passage 6 to the right end of the pillow 3. Similarly, if the subject lies on his right side and his head rests on the left side of the pillow, the left valve-chamber 1 is closed and the air will flow through the passage 7, the right valve chamber 2 and the passage 5 to the left end of the pillow 3. If the subject lies on his back and his head is located in the central part of the pillow 3, the valve-chambers 1 and 2 will be partially closed, their cross sections will be reduced and the air will flow to the right end and the left end of the pillow in the quantities which are proportional to the offset of the subject's head from the center of the pillow. Thus, in any position of the subject's head the air will be directed exactly toward the subject's face.

In the second embodiment of the invention, the air flows through one of the three passages 5, 6 and 14. If the subject lies on his right side and his head is located on the left side of the pillow, the valve-chambers 1 and 10 are closed and the air will flow through the passage 7, the central valve-chamber 9, the tee 13, the right valve-chamber 2 and the passage 5 to the left end of the pillow 3. When the subject lies on his left side and his head is located on the right side of the pillow 3, the valve-chambers 2 and 11 are closed and the air will flow through the passage 7, the central valve-chamber 9, the tee 13, the left valve-chamber 1 and the passage 6 to the right end of the pillow 3. Finally, when the subject lies on his back and his head is located in the central part of the pillow, the central valve-chamber is closed and the air will flow through the passage 7, the valve-chambers 10 and 11 and the passage 14 to the central part of the pillow. As can be seen from the drawings, the passages 5, 6 and 14 at their ends are somewhat bent to direct the air exactly toward the face of the subject in his respective positions.

The inlet passage 7 can be connected with a central or local system of ventilation of any type. In the local system the source of air can be a turbine blower of required power.

For increasing the sensitivity of the device, the valve-chambers should be arranged between an upper pillow of a set of two thin pillows, instead of under one thick pillow.

At least the end portions of the passages 5, 6 and 14 are flexible (for example formed as bellows, elastic pipes. etc.) for adjusting the exact location of the outlets of the passages relative to the pillow and therefore relative to the subject, in dependence upon the individual preferences and habits of the subject. For example, if in deviation from the above described head displacement of a subject during his turning to his right side or left side, his head shifts to the left side of the pillow when he turns to lie on his left side and vice versa, the passages can be bent to locate their outlets opposite to the arrangement shown in the drawings.

On the other hand, another solution can be proposed. All passages can be arranged so that all outlets act over the whole surface of the pillows from above.

In the embodiment shown in FIGS. 5, 6, and 7 the passages 5 and 6 have a common passage portion 15 in which air streams from both passages interact. The passage portion 15 has an outlet pipe 14. When air flows only through one of the passages 5 or 6 while the valve-chamber of the other passage is closed, the air flows through a further portion of the same passage 5 or 6 through the passage portion 15. If both passages supply the air from their valve-chambers, a resultant air stream is formed in the passage portion 15 and flows out through the outlet pipe 14. If the air streams from the passages 5 and 6 are identical, the resultant air stream flows out centrally of the outlet pipe 14. If the air streams are not identical, the resultant air stream deviates toward a weaker air stream and is distributed between the central and side outlets.

Air supply to the inventive device can be provide by a diaphragm pump which for example is used for home fish tanks. The supplied air can be preliminarily cleaned from dust, etc.

The invention is not limited to the details shown since various modifications and structural changes are possible without departing in any way from the spirit of the present invention.

What is desired to be protected by Letters of Patent is set forth in the appended claims.

I claim:

1. An air supply device to be used for ventilation in the vicinity of a subject's face while subject is sleeping on a pillow, comprising:
    a plurality of normally inflated valve-chambers arranged to be located under respective sides of a pillow and formed so that when a subject's head rests on at least one of said valve-chambers, said at least one valve-chamber is deflated while another of said valve-chambers not supporting the subject's head remains inflated;
    means for supplying air to said valve-chambers; and
    a plurality of passages, at least one passage extending from each of said valve-chambers, each of said passages having an outlet, each outlet being at the opposte side of the pillow from its associated valve-chamber, and being directed across the pillow towards the subject's face such that when the subject's head rests on at least one of said valve-chambers and the latter is deflated, the air supplied from said supplying means to said valve-chambers exits from at least one of said inflated valve-chambers, through its associated passage to its outlet, thereby directing air toward the face of the subject.

2. An air-supplying device as defined in claim 1, wherein said plurality of passages include two passages each having one of said outlets, said two passages and their associated outlets arranged such that one of said outlets is located at a right end of the pillow, and the other of said outlets is located at a left end of the pillow.

3. An air-supplying device as defined in claim 1, wherein said plurality of passages include three passages, each having an outlet, said three passages and their associated outlets being arranged such that an outlet is located at a right end, a left end and centrally of the pillow.

4. An air-supplying device as defined in claim 2, wherein said valve-chambers and said passages are arranged so that when the subject's head rest centrally of the pillow, air is supplied through both of said outlets, and such that the two of said valve chambers connected with said two passages are partially inflated.

5. An air-supplying device as defined in claim 3, wherein said passages comprise two side passages and one central passage provided with said right end, left end and central outlets respectively, said valve-chambers comprising two side valve-chambers and one central valve chamber connected with said passages respectively so that when the subject's head rests on a central area of the pillow the air is supplied by said supplying means through said two side passages.

6. An air-supplying device as defined in claim 1, wherein at least the end portions of said passages are adjustable so as to permit adjustment of the positions of said outlets relative to the pllow and therefore relative to the subject's head.

7. An air supplying device as defined in claim 1, wherein said valve-chambers are formed as air-impermeable bags.

8. An air supplying device as defined in claim 1, wherein at least two of said passages intersect one another and have a common passage portion at the point of intersection, said common passage portion being provided with an additional outlet.

9. A method of supplying air to a subject whose head rests on a pillow, comprising the steps of
providing a plurality of normally inflated valve-chambers connected with an air supply means and with a plurality of passages each having an outlet located at a side of the pillow opposite its associated valve-chamber and directed across the pillow towards the face of the subject;

placing the valve-chambers under different areas of a piloow so that when the subject's head rests on one area of the pillow and therefore on one of the valve-chambers, the latter is deflated while another of the valve-chambers remains inflated and thereby supplying air to its associated passage to discharge the air through said outlet of said associated passage substantially toward the face of the subject.

* * * * *